United States Patent
Rullo et al.

[11] Patent Number: 5,964,699
[45] Date of Patent: Oct. 12, 1999

[54] SURGICAL SUPPORT APPARATUS WITH A Z-SHAPE RAKE PLATE

[75] Inventors: Janice Lee Rullo, Mayfield Heights; William John Koteles, Broadview Heights, both of Ohio

[73] Assignee: Rultract, Inc., Cleveland, Ohio

[21] Appl. No.: 09/235,840

[22] Filed: Jan. 22, 1999

Related U.S. Application Data

[60] Provisional application No. 60/072,274, Jan. 23, 1998, provisional application No. 60/072,366, Jan. 23, 1998, provisional application No. 60/072,240, Jan. 23, 1998, and provisional application No. 60/072,273, Jan. 23, 1998.

[51] Int. Cl.⁶ .................................................. A61B 17/02
[52] U.S. Cl. .......................................... 600/228; 600/217
[58] Field of Search .................................. 600/228, 229, 600/217, 219, 224, 231, 232

[56] References Cited

U.S. PATENT DOCUMENTS

| | | | |
|---|---|---|---|
| 3,643,655 | 2/1972 | Peronti | 600/228 |
| 4,622,955 | 11/1986 | Fakhrai | 600/228 |
| 4,627,421 | 12/1986 | Symbas et al. | 600/232 |
| 4,726,356 | 2/1988 | Santilli et al. | 600/232 |
| 4,813,401 | 3/1989 | Grieshaber | 600/231 |
| 4,829,985 | 5/1989 | Couetil | 600/232 |
| 5,025,779 | 6/1991 | Bugge | 600/232 |
| 5,616,117 | 4/1997 | Dinkler et al. | 600/232 |
| 5,667,481 | 9/1997 | Villalta et al. | 600/219 |

*Primary Examiner*—Paul J. Hirsch
*Attorney, Agent, or Firm*—Renner, Otto, Boisselle & Sklar, P.L.L.

[57] ABSTRACT

A first embodiment of a surgical retractor includes a Z-shape rake plate, one or more rakes for applying a retractor force to a portion of a patient's body, and pivoting mounting means for mounting the rakes to the rake plate. Means are provided to adjust the extension of the rakes relative to the rake plate, and various connections are provided for connecting the rakes to the rake plate. The rake plate is Z-shape to facilitate placement relative to a surgical cavity of a patient. A method of holding open a surgical cavity includes the placing of rakes relative to the cavity and adjusting the position of the respective rakes relative to the rake plate to thereby retract the portion of the patient's body and provide access to the surgical cavity.

18 Claims, 5 Drawing Sheets

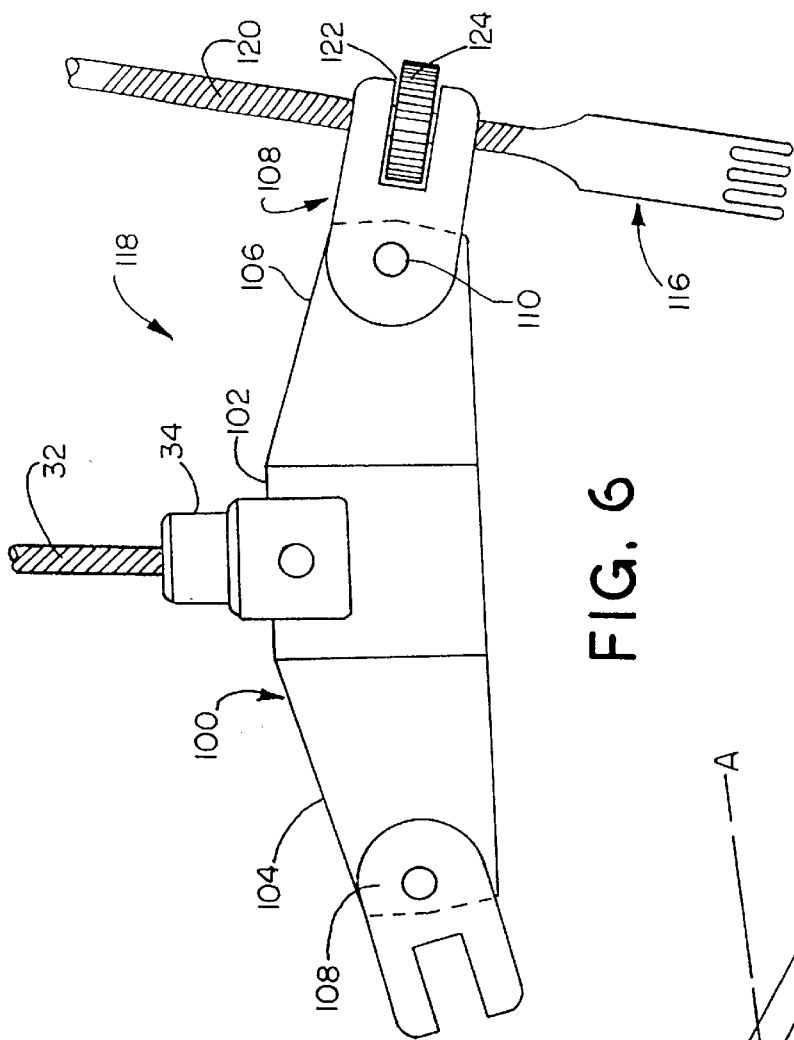
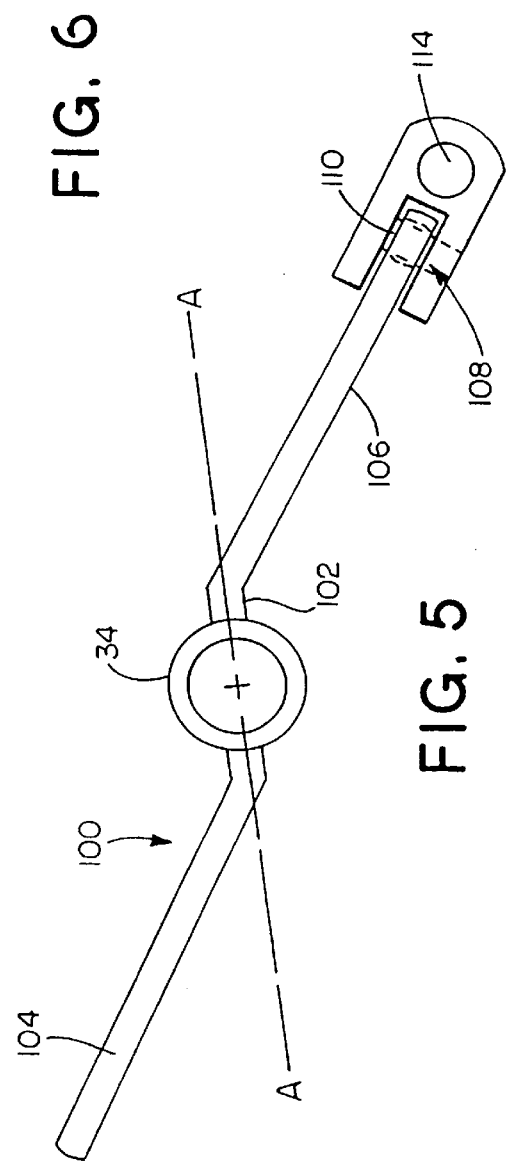
FIG. 6
FIG. 5

SURGICAL SUPPORT APPARATUS WITH A Z-SHAPE RAKE PLATE

CROSS-REFERENCE TO RELATED APPLICATIONS

Reference is hereby made to the following applications co-pending herewith, the disclosure of each of which is hereby incorporated by reference in its entirety: SURGICAL SUPPORT APPARATUS WITH SPECIALIZED RAKES, Ser. No. 60/072,366 filed Jan. 23, 1998; SURGICAL SUPPORT APPARATUS WITH CROSS BAR SUPPORT AND EXTENSION FOR RETRACTOR APPARATUS, Ser. No. 60/072,240 filed Jan. 23, 1998; SURGICAL SUPPORT APPARATUS WITH ADJUSTABLE RAKE AND ADJUSTABLE CABLE LIFTING DISK, Ser. No. 60/072,273 filed Jan. 23, 1998, and SURGICAL SUPPORT APPARATUS WITH A Z-shape RAKE PLATE, Ser. No. 60/072,274 filed Jan. 23, 1998. The present application claims benefit under 35 U.S.C. 119 from U.S. patent applications Ser. Nos. 60/072,274, 60/072,366, 60/072,240, and 60/072,273.

FIELD OF THE INVENTION

The present invention relates generally to surgical instruments for holding and elevating body parts and/or for maintaining a clear opening to a body area during surgery, particularly thoracic surgery. More specifically, the present invention relates to support apparatus upon which surgical devices, such as retractors and the like, may be operably mounted.

BACKGROUND OF THE INVENTION

In the performance of surgery in the chest cavity, generally referred to as thoracic surgery, it is desirable to hold open the surgical cavity to provide access to the organ or body part upon which the surgery is being performed. This is especially important in the case of cardiac surgeries. An early example of a surgical retractor for use in coronary bypass surgical procedures which include dissection of the internal mammary artery is disclosed in U.S. Pat. No. 4,622,955, which is incorporated herein by reference.

In the device of U.S. Pat. No. 4,622,955 plural rakes which engage the body and retract the surgical cavity formed by a midsternotomy are relatively fixedly positioned with respect to each other from a rod. The rod may be elevated or lowered as desired. However, there is no adjustment for the rakes relative to the rod, to each other or to the surgical cavity. Furthermore, the rakes are generally small having sharply pointed tips and are generally designed to be employed in pairs for the purpose of retracting one side of a sternum which has been split by a midsternotomy. The device of U.S. Pat. No. 4,622,955 cannot provide the support required for other procedures which have been recently developed as alternatives to the midsternotomy approach to the coronary bypass, and it is not adapted for use in reoperative midsternotomy procedures.

It is well-known and appreciated that in surgical procedures, time is of the essence, and delays associated with adjustments of support equipment are unwanted. Additionally, during certain procedures, it may be desirable to impose or to change a biasing force on a body portion which is undergoing a surgical procedure or treatment. Further, it is desirable to minimize the number of personnel required to assist in the performance of a surgical procedure, to minimize the number of personnel who must enter the sterile field, and to minimize the tasks, such as holding a retractor, of personnel during surgical procedures. Further, it is desirable to have available to the surgeon instruments appropriately adapted to each type of procedure.

Coronary Bypass Surgery: The Midsternotomy

Coronary bypass surgery, in which the internal mammary artery is harvested from the chest wall and used for anastomosis of a vessel to bypass poorly functioning coronary arteries, has been performed thousands of times and has become an almost routine procedure for cardiac surgeons. Since the inception and throughout the development of the procedure, coronary bypass surgery has required a midsternotomy to provide access to the heart and coronary arteries. In the midsternotomy, an initial incision is made from the manubrium of the sternum to a point toward the xiphoid. Next, the sternum is split down the middle by means of a reciprocating sternal saw in order to provide access to the coronary arteries and the internal mammary artery. It has been estimated that in 1988, some 350,000 midsternotomy procedures were performed for coronary bypass surgery.

In performing the coronary bypass procedure, following the midsternotomy, it is necessary to retract one side of the split sternum in order to gain access to the thoracic cavity, and particularly to the internal mammary artery. Either the left or right internal mammary artery may be harvested for the bypass, so either side of the chest may need to be retracted. Retractors have been developed in order to provide the requisite retraction of the split sternum. An early example is disclosed in U.S. Pat. No. 4,622,955. The RULTRACT® internal mammary artery retractor is a more advanced retractor which has been developed to provide left or right internal mammary artery exposure in the undersurface of the chest wall. The RULTRACT® internal mammary retractor has been extensively used in coronary bypass surgery. The RULTRACT® retractor is not limited to coronary bypass surgery, having been used in various other thoracic surgical procedures, such as lung reduction and pericardial drainage.

The RULTRACT® internal mammary retractors include a rake plate and two or possibly three rakes. Most frequently, in use the two rakes are applied to one side of the opening formed by a midsternotomy and the rake plate is attached to a lifting device. The lifting device lifts the rake plate and the rakes, applying an upward and outward retraction to the sternum by which the surgical cavity is opened. The sternum is securely held in the open position when the lifting device is locked in position. This exposes the entire course of the mammary artery from its origin to its bifurcation, allowing its dissection. The rakes in the conventional retractor have a relatively small radius of curvature and have quite sharp tips to provide a secure attachment to the sternum. With the sternum securely held in the open position, the coronary artery dissection may then be carried out by the surgeon. In the standard midsternotomy, the retractor provides good exposure and allows the surgeon sufficient access for the dissection of the mammary artery.

After the coronary artery has been harvested, the RULTRACT® retractor is removed and a sternal retractor is placed in the chest and the grafting and anastomoses is performed. Closure is normally accomplished in this procedure by applying wires or staples to the sternum to hold it together in the properly aligned position for healing.

The midsternotomy is a highly invasive procedure, and much of the difficulty in recovering from a coronary surgical procedure involving a midsternotomy is due to the trauma resulting from the midsternotomy rather than to any trauma inflicted upon the coronary arteries or other thoracic organs and structures. As a result, a need has been identified for a less invasive procedure which will provide the surgeon with access to the coronary and internal mammary arteries with a minimum of trauma to the thoracic region.

The Mid-Cab, A Less Invasive Procedure

A less invasive procedure which has been developed to provide access to the mammary artery and the coronary arteries for coronary bypass surgery is known as the mid-cab or minimally invasive technique. In the mid-cab, an incision is made between the third and fourth rib, in the third intercostal region. The fourth rib is released from the sternum, and the incision is retracted downward by attaching a retractor rake to the fourth rib. A second retractor rake is next attached to the third rib, which is retracted upward and in the cranial direction. With access thus provided to the third rib and in the direction of the upper chest, the surgeon is able to create an opening from the third rib to the first rib or subclavian region. Via this opening, the surgeon is provided with access to the mammary artery, which is progressively dissected from the chest wall as the opening is progressively advanced toward the first rib. With the development of this procedure, a need has been identified for more advanced retractors specially adapted to the mid-cab procedure, and particularly for a retractor which can simultaneously retract the third and fourth ribs in different directions.

It is well-known among cardiac surgeons that the position of the internal mammary artery in the chest is variable from patient to patient. For this reason, during the mid-cab procedure, it is sometimes necessary for the surgeon to manipulate the chest wall to provide adequate access to the mammary artery. The surgeon may have to either elevate or depress the chest wall in the region of the first rib in order to gain access to the mammary artery so that it can be dissected in this procedure. Thus, a need has been identified for devices which can assist the surgeon in the less invasive mid-cab procedure, particularly including a retractor capable of two-direction retraction at the site of the intercostal incision and devices for providing elevation and/or depression of the clavicle and first rib region of the chest wall.

Reoperative Coronary Bypass Surgery

As coronary surgery has become increasingly prevalent and postoperative coronary rehabilitation more successful, a larger number of patients are surviving longer than the expected patency of their graft conduits. This has resulted in an increasing number of patients having to undergo a second coronary bypass procedure. The second, or reoperative, procedure has sometimes been referred to as a "re-do" procedure. Unfortunately, the re-do midsternotomy is neither as simple nor as safe as the initial procedure. This is primarily due to the scarring and resultant adhesions which develop between the internal side of the sternum and the underlying organs and tissues of the thoracic cavity following the initial midsternotomy. When the re-do midsternotomy is performed by essentially repeating the steps of the initial procedure, an increase in morbidity and mortality has been observed. Thus, a need has arisen for an alternative procedure.

An alternative procedure which has been adapted to coronary surgery in order to avoid the dangers of the re-do midsternotomy is known as a xiphoid entry. In the xiphoid entry, an initial incision is made along the scar from the previous midsternotomy to a point midway between the xiphoid and the umbilicus. The old sternal wires are removed. The xiphoid process is excised. A single retractor rake is applied to the caudal end of the sternum and the sternum is firmly retracted in an anterior and cranial direction. This allows the surgeon to directly visualize the anterior retrosternal space, so that the retrosternal adhesions can be taken down. The surgeon progressively takes down the adhesions toward the subclavian, until the sternum is freed from the underlying organs. Once this is done, the retractor may be removed and the sternum divided with a reciprocating sternal saw as in the original procedure.

During the retraction, particular care must be exercised since, first, the quite sharp rake tips of the standard retractor are applied directly to the lower end of the sternum from which the xiphoid process was excised, and second, a very strong lifting force is required to elevate the entire sternum. The possibility of unintended trauma to the sternum exists. A second problem which has been experienced with the procedure described above is that the entire retractor plate and the extra, non-used rake must be suspended in a central location in the operating field, further obstructing the work area with its already limited available space. A third problem is that due to the rake plate and various parts attaching it to the lifting apparatus, the retraction force applied to the sternum is not transmitted in a simple straight line from the lifting apparatus to the sternum. Thus, a need has been identified for a rake which is more appropriately adapted to the xiphoid entry in a re-do coronary bypass procedure.

In the procedures described in the foregoing and in additional thoracic surgical procedures, the surgeon may be required to adapt the support apparatus for retraction of the patient's body in several directions at once. In such an instance, a single retractor held by a single support device may not be sufficient to provide the retraction required by the surgeon. Furthermore, it may be helpful to the surgeon to combine various embodiments of retraction devices in order to adequately obtain the retraction required.

Accordingly, there is a strong need in the art to provide for surgical retractor rake apparatus with which to facilitate the development and implementation of new surgical procedures, particularly less invasive procedures such as the mid-cab coronary artery bypass procedure, and for more radical thoracic procedures, such as a lung reduction or other procedure.

SUMMARY OF THE INVENTION

The internal mammary artery is known to thoracic surgeons to not have a well-defined position in all patients, but rather to have a highly variable position in the thoracic cavity. As a result, the procedure for accessing and harvesting a portion of the internal mammary artery must be quite flexible in a mid-cab procedure. The present invention relates to retraction apparatus which may be selected and quickly implemented as required in an individual surgical procedure depending on the particular patient's needs. The system allows the surgeon to perform a less-invasive procedure while maintaining the option to easily switch to the standard midsternotomy in the event of unforeseen difficulties. When the RULTRACT® retractor system and the device of the present invention are employed, the switch to the midsternotomy may be made with a minimum change of retraction equipment.

According to an embodiment of the invention, a surgical retractor includes a rake plate, at least one rake mounted with respect to the rake plate for applying a retractor force to a portion of a patient's body, in which the rake plate has a generally Z-shape structure. The surgical retractor of this embodiment further includes means for adjusting the extension of the rakes relative to the rake plate.

According to another embodiment of the invention, a surgical retractor includes a Z-shape rake plate having a center portion and respective end portions, a mounting device to mount a respective rake in relative proximity to the respective end portions of the rake plate, and a clip for coupling a rake in relative proximity to the center portion of the rake plate. The surgical retractor of this embodiment may further include means for adjusting the extension of the rakes relative to the plate.

According to an aspect of the present invention, a method of holding open a surgical cavity includes the steps of attaching at least one rake to a Z-shape rake plate, placing the at least one rake relative to the cavity, and adjusting the extension of the at least one rake relative to the rake plate.

To the accomplishment of the foregoing and related ends, the invention then comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 5 is a top plan view of a rake support plate of FIG. 3 with a pivotable pivot clamp mounted thereon in accordance with an embodiment of present the invention.

FIG. 6 is a front elevational view of a Z-shape rake plate with an adjustable rake mounted thereon in accordance with an embodiment of the present invention.

DETAILED DESCRIPTION

Figure 1:
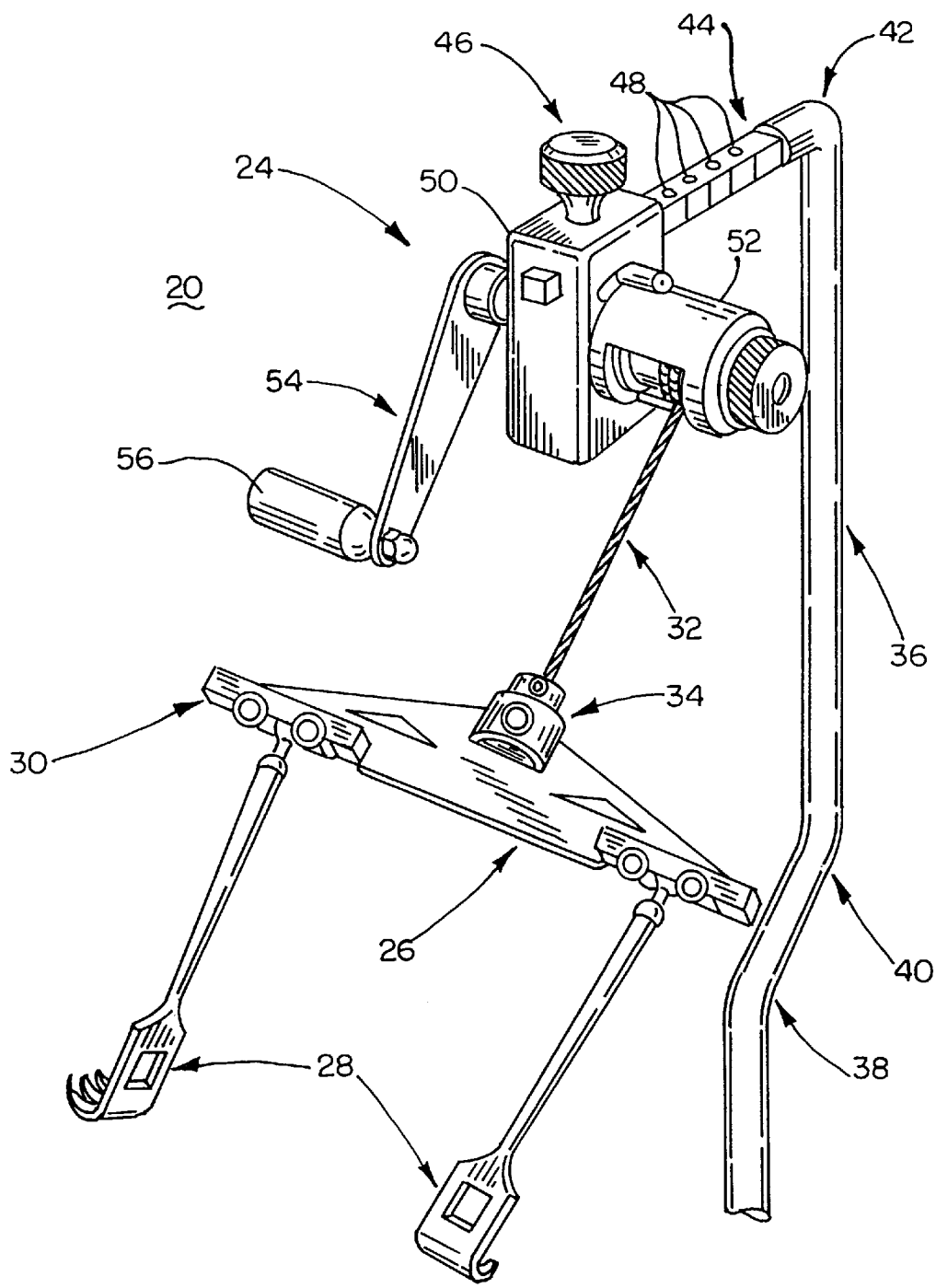
FIG. 1 is a perspective view of a conventional Rultract® surgical retractor.

The present invention will now be described with reference to the drawings wherein like reference numerals are used to refer to like elements throughout. As mentioned above, the present invention relates to surgical instruments for holding open a body part during surgery, for example, to maintain open and clear a surgical cavity during surgery, particularly including cardiac surgery or other thoracic surgery. In all embodiments described hereinafter, the preferred material of construction is stainless steel, preferably 304 stainless steel, which has good strength and sterilization characteristics and is resistant to corrosion even after many cycles of use, cleansing and sterilization. If desired, other materials may be used which have characteristics suitable to the invention.

Referring to FIG. 1, a conventional RULTRACT® retractor and surgical support assembly 20 are shown. The RULTRACT® retractor includes a ratcheting lifting device 24, a rake plate 26, at least one rake 28 for applying retraction to a patient's body, and pivoting mounting means 30 for mounting the rakes 28 to the rake plate 26. The rake plate 26 is attached to the ratcheting lifting device 24 by a cable 32. The cable 32 is attached to the rake plate 26 by a pivot hub connector 34.

The rake plate 26 and the rakes 28 associated therewith may be raised or lowered via the cable 32, which is connected to the ratcheting lifting device 24. As described below, the RULTRACT® system preferably includes the ratcheting lifting device 24, although other lifting devices could be used. Preferably, a pivot hub connector 34 allows the rake plate 26 to rotate relative to the cable 32 to facilitate positioning of the rakes 28 relative to the surgical cavity of the patient without twisting the cable 32, which could result in a torque applied to the retractor rake plate 26, which undesirably could be transmitted to the patient's body.

In the conventional RULTRACT® retractor assembly 20, the ratcheting lifting device 24 is mounted on a support pole 36. Although not shown in FIG. 1, the support pole 36 is mounted at its lower end to a surgical table by conventional means. Preferably, the support pole 36 includes bends 38 and 40 which dispose outward the portion of the support pole 36 which is above the level of the surgical table so as to provide additional space in the surgical field around the patient. At the upper end of the pole 36, is a bend 42, preferably right-angled bend, connecting the support pole 36 to a horizontally extending portion 44. The horizontally extending portion 44 extends outwardly above the patient, so that the retraction force is applied at least partially in an upward direction. Since the ratcheting lifting device 24 is not aligned with the patient's midline, the retraction is applied partially, outwardly, laterally with respect to the patient.

In this embodiment, the ratcheting lifting device 24 is mounted on the horizontal extension 44. The lifting device 24 is provided with a securing bolt 46 by which the lifting device 24 is securely positioned on the extension 44. To facilitate quick and sure positioning of the lifting device 24 on the extension 44, a plurality of bores 48 are provided, into which an end of the securing bolt 46 may be inserted. The bores 48 allow for precise horizontal adjustment of the position of the lifting device 24 relative to the patient and the surgical field.

The ratcheting lifting device 24 preferably includes a winching assembly 50 for reeling in the cable 32. The cable 32 is attached to and preferably is reversibly wrapped around a spool (not shown) extending outwardly from the winching assembly 50. The spool around which the cable 32 wraps is preferably partially enclosed by a housing 52. The opposite end of the spool is attached to, and the winching assembly 50 is actuated by, the crank arm 54 and crank handle 56, in conventional fashion.

In the following description of the present invention, like reference numbers refer to like parts. The lifting device 24 and support arm used in the present invention are preferably essentially the same as the conventional assembly described above and will not be further described except as necessary to indicate the functioning of the present invention relative thereto.

Figure 2:
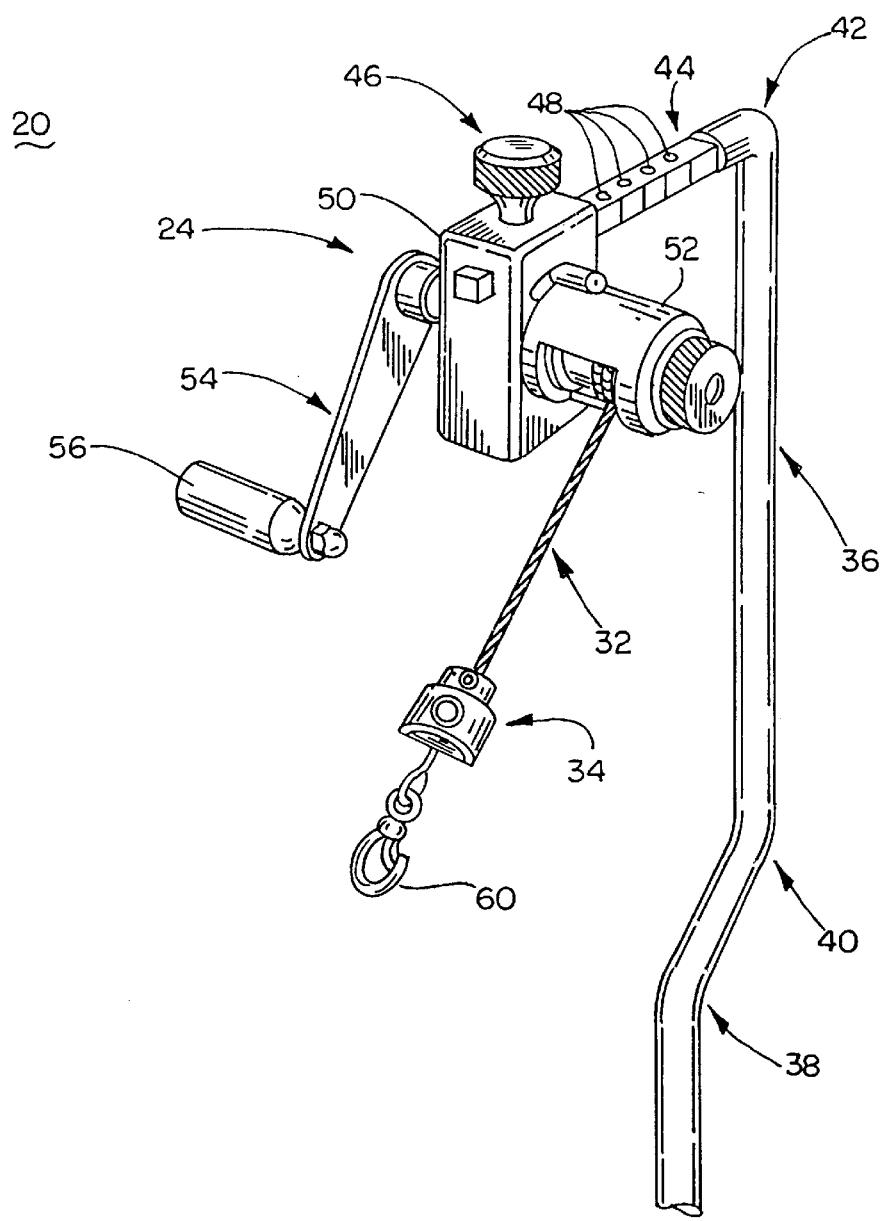
FIG. 2 is a perspective view of a conventional Rultract® retractor support and lifting apparatus with a swiveling hub and snap clip for attaching a rake plate or individual rakes.

Preferably, in the present invention, the ratcheting lifting device is similar to the ratcheting lifting device 24 shown in FIG. 1 and available from RULTRACT, INC., Cleveland, Ohio. Referring to FIG. 2, in an alternative embodiment of the surgical support assembly of the present invention, the ratcheting lifting device 24 has the cable 32 attached thereto, as described above with reference to FIG. 1. As shown in FIG. 2, the free end of the cable 32 may have attached thereto a pivot hub connector 34 and a snap ring 60. The snap ring 60 is preferably used for attaching the lifting device to the Z-shape rake plate of the present invention. The snap ring 60 provides a secure, but quickly releasable attachment between the lifting device 24 and the rakes or retraction apparatus used with the present invention. Other quick-release devices known in the art may be substituted for the snap ring 60.

Preferably, and in the embodiments shown in FIGS. 3–6 of the drawings, the Z-shape rake plate of the present invention replaces the rake plate shown in FIG. 1. In the preferred embodiment the cable 32, suspended from the lifting and supporting system, is attached to a hub connector such as the pivot hub connector 34 in FIG. 1.

Figure 3:
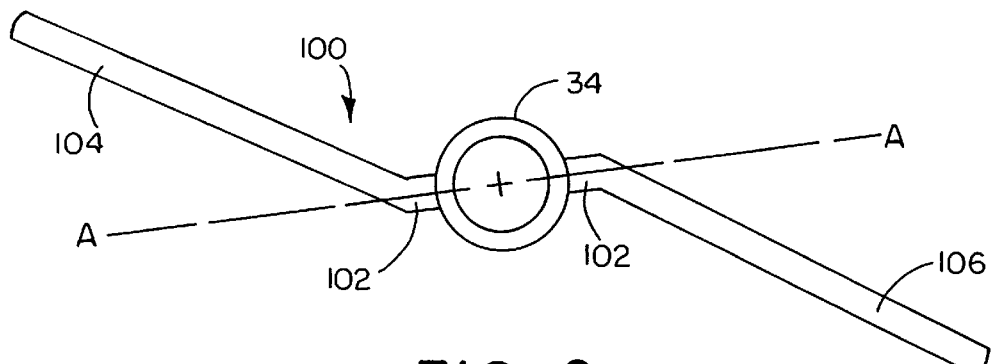
FIG. 3 is a top plan view of the Z-shape rake plate in accordance with an embodiment of the present invention.

Referring now to FIG. 3, which is a top plan view of a Z-shape rake plate 100 for use in the surgical retractor of the present invention, the preferred Z-shape configuration of the rake plate 100 in the present invention is shown. The Z-shape rake plate 100 preferably includes a central portion 102, upon which the centrally disposed pivot hub connector 34 is mounted. Alternatively, the central portion 102 may simply have an opening into which the snap clip 60 or equivalent quick-connect attaching device may be inserted. The pivot hub connector 34 is connected to the cable 32 and thence to the support structure, such as that available from RULTRACT, INC. shown in FIG. 1. The Z-shape rake plate 100 may be raised or lowered via the cable 32 as disclosed above. Preferably, the pivot hub connector 34 allows the rake plate 100 to rotate relative to the cable to facilitate positioning of the rakes relative to the surgical cavity of the patient without twisting the cable 32.

As further shown in FIG. 3, the Z-shape rake plate 100 includes arms 104 and 106. Preferably, the arms 104, 106 are equivalent to each other except as to the angle at which they are disposed, and both are preferably integrally attached to the central portion 102.

Figure 4:
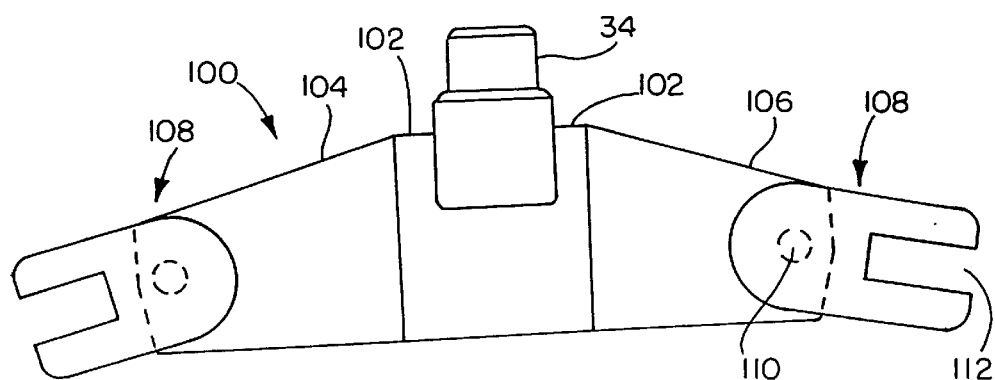
FIG. 4 is a front elevational view of the Z-shape rake plate of FIG. 3.

Referring now to FIG. 4, which is a side elevational view of the Z-shape rake plate 100 of the present invention, a pair of pivot clamps 108 are shown attached to the rake plate 100. As shown in FIG. 4, the pivot clamps 108 are each pivotably mounted on a pivot pin 110. The pivot clamps 108 include slots 112 for mounting rake adjusting nuts, which will be described in more detail below. Preferably, the orientation of the slots 112 is the same as the pivot pin 110. In the present description, the orientation of both the slot 112 and the pin 110 is referred to as horizontal.

FIG. 5 shows a top plan view of the Z-shape rake plate 100 of the present invention including the pivot clamps 108 mounted thereon. As shown in FIG. 5, the pivot clamps 108 include a centrally located rake mounting opening 114 through which the rakes will be inserted. The rake mounting opening 114 preferably is vertically oriented and is preferably aligned perpendicularly with respect to the pivot pin 110, the opening in the pivot clamps 108 through which the pivot pins extend, and the slots 112.

FIGS. 4 and 5 show two views of the pivot clamp 108 mounted on the rake plate 100, but without a rake 116. The pivot clamp 108 preferably is pivotably mounted on the rake plate 100 by a pin 110, shaft, bolt or other equivalent means.

As is illustrated in FIGS. 3 and 5, the angle of the arms 104, 106 of the rake plate relative to a vertical plane A—A passing through the center of the pivot hub connector 34 and the central portion 102 is about 30 degrees. Preferably, the pivot clamps 108 are permitted a range of pivoting movement on the order of at least about 30 degrees. However, it will be appreciated that the respective angular relationships may be more or less than those mentioned and illustrated.

The Z-shape rake plate 100 provides additional flexibility in surgical procedures due to the offset between the respective rakes. Such a rake plate may be useful in other thoracic procedures.

With reference to FIG. 6, which is similar to FIG. 4 in being a side elevational view of the Z-shape retractor 118 of the present invention, the rake plate 100 with a rake 116 operably mounted in the rake mounting opening 114 is shown. According to an embodiment of the present invention, the surgical retractor 118 includes the Z-shape rake plate 100, and at least one rake 116, for applying retractor force to a body. Preferably, two rakes 116 are mounted on the Z-shape rake plate 100. Only one rake and adjusting means will be shown and described, since the rakes are preferably equivalent. The rake or rakes 116 are preferably mounted outwardly with respect to the central portion 102 of the rake plate 100.

Preferably, as shown in FIG. 6, the rake 116 includes a threaded portion 120, and the pivot clamp 108 includes an opening 122 for receiving a threaded nut 124. The threaded nut 124, when mounted with the rake 116 is threadingly engaged with the threads of the threaded portion 120. Rotation of the nut 124 causes the rake 116 to be moved up or down with respect to the pivot clamp 108 and therefore with respect to the rake plate 100.

It is noted that the rake 116 in FIG. 6 is shown schematically. Any rake having a threaded shaft may be used with the presently described embodiment of the present invention. It is further noted that other conventionally known rakes may be swivelably mounted on the Z-shape rake plate of the present invention by known means, such as that shown in FIG. 1, rather than being capable of vertical adjustment as is the rake shown in FIG. 6.

Figure 7:
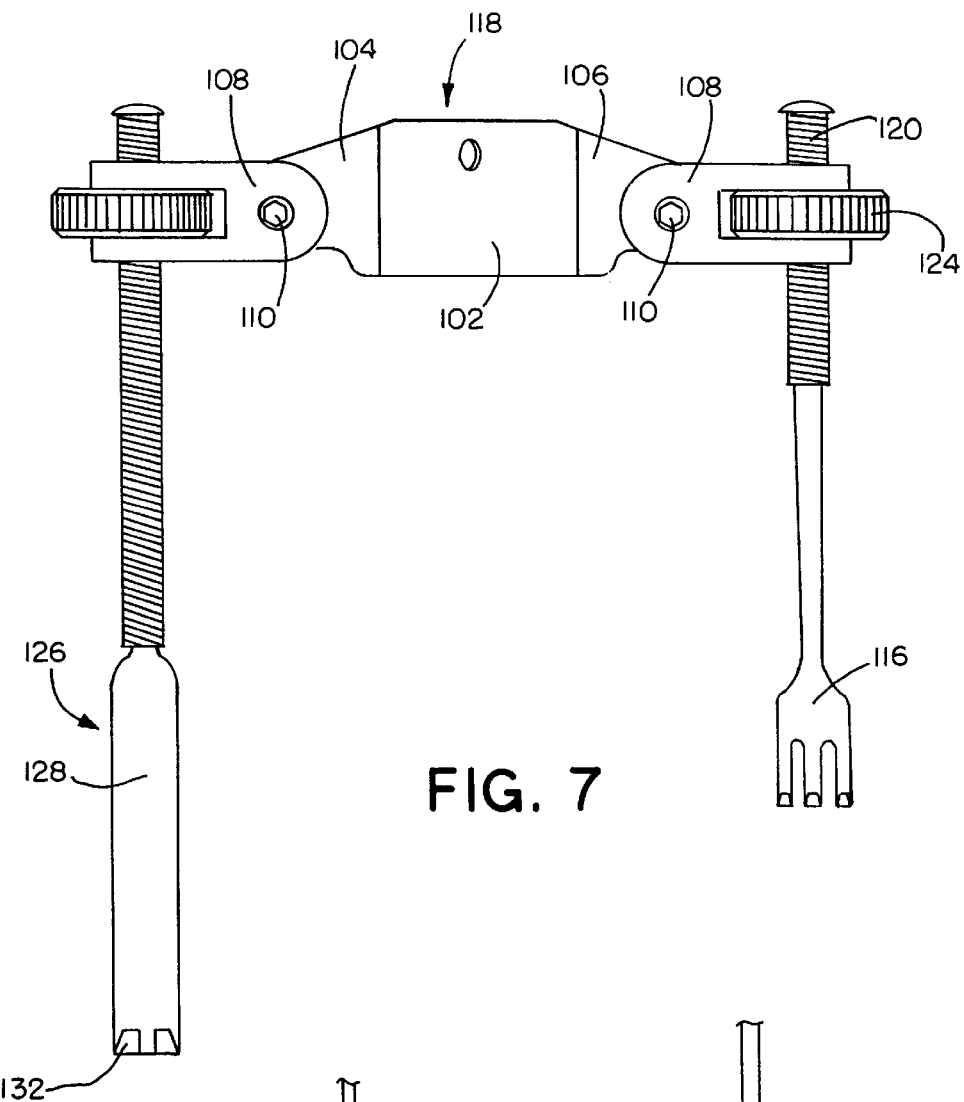
FIG. 7 is a front elevational view of a Z-shape rake plate with two adjustable rakes mounted thereon in accordance with another embodiment of the present invention.
Figure 8:
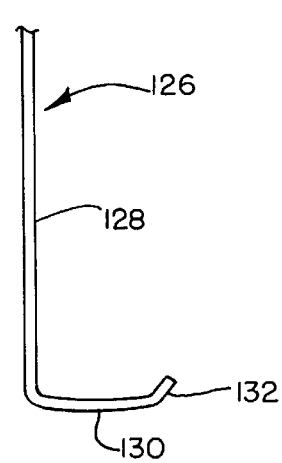
FIG. 8 is a side elevational view of the L-shaped sternal rake in accordance with the present invention.
Figure 9:
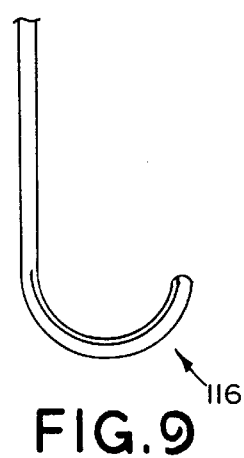
FIG. 9 is a side elevational view of the lower portion of the rib rake in accordance with the present invention.

The Z-shape retractor 118 is preferably used in a less-invasive procedure such as the mid-cab. FIG. 7 is a front elevational view of the Z-shape retractor 118, including an L-shaped sternal rake 126 and a rib rake 116. The rake portion of the rib rake 116 has been more fully described in the application entitled A SURGICAL SUPPORT APPARATUS WITH SPECIALIZED RAKES, Ser. No. 60/072,366, which has been incorporated herein by reference. FIG. 9 is a side elevational view of the lower portion of the rib rake 116. FIG. 8 is a side elevational view of the L-shaped sternal rake 126. As is shown in FIGS. 7 and 8, the L-shaped sternal rake 126 includes a flat portion which preferably includes a portion 128 which extends vertically downward about 3 inches (about 7.5 cm), includes a bend of about 90° connecting the vertically downward portion 128 to a horizontally extending portion 130, and ends in a slightly upward extending tip 132. The bend may be slightly less than 90°. The horizontally extending portion 130 is preferably about ¾ inch to about 1 inch (about 1.8 cm to about 2.5 cm) in length. The upwardly bent tip 132 is preferably at an angle of about 30° upward relative to the horizontally extending portion 130, and is preferably about ⅛ inch (about 3 mm) long. The L-shaped sternal rake 126 is designed to fit laterally in an intercostal region and to support the sternum laterally, i.e., from the patient's side. The upwardly bent tip 132 is preferably divided into two rake teeth. The rake teeth on the tip 132 differ from the rake teeth in being shorter and less sharp. By use of the term shorter, it is intended that the length of the separations between the rake teeth on the tip 132 is smaller than in other rakes.

Similarly, the surgical retractor of this embodiment may include other means for adjusting the extension of the rakes relative to the Z-shape rake plate, such as a compression clamp. However, the foregoing description provides an adjustment device which is simple to use and is easy to clean and sterilize, yet still provides a wide range of adjustments for use during a variety of surgical procedures.

A method for using the foregoing surgical retractor in a surgical procedure will now be described. The preferred method of holding open a surgical cavity includes at least the following steps. A surgical incision is made in a patient's body to create a surgical cavity. A first rake and a second rake are attached to a Z-shape rake plate. The first rake is placed in the surgical incision relative to the surgical cavity. The length of the first rake is adjusted relative to the rake plate. The second rake, also attached to the Z-shape rake plate, is placed in the surgical incision relative to the surgical cavity at a position for cooperation with the first rake. The length of the second rake is adjusted. The Z-shape rake plate, together with the attached rakes, is retracted by the lifting device, whereby a portion of the patient's body is retracted and the surgeon is provided improved access to the surgical cavity. Thus, the Z-shape rake plate provides assistance in opening a surgical cavity and providing enhanced access and visualization to the surgeon.

The surgical procedure may include accessing the internal mammary artery, for example, in a coronary bypass procedure. In the new technique known as the mid-cab procedure, the internal mammary artery is accessed for harvesting by a minimally invasive surgical technique which involves making an incision in the third, fourth or fifth intercostal region, as described in the background of the invention. Since an incision at this location provides limited access to the thoracic cavity, the surgical site must be retracted as much as possible. it is desirable to minimize the amount of equipment used in achieving the desired degree of retraction in order to keep clear the surgical field. The Z-shape rake plate of the present invention, by providing an offset position to the rakes mounted thereon, is particularly suited to achieving the desired degree of retraction by means of a single retractor, thereby keeping the surgical field as uncluttered as possible and providing the cardiac surgeon with full access to the thoracic cavity.

With the L-shaped sternal rake and the rib rake on the Z-shape rake plate, the surgeon is enabled to perform an incision in the third, fourth or fifth intercostal region, place the rib rake around one rib adjacent the incision in the cranial direction, and place the L-shaped sternal rake laterally in the intercostal region with the horizontally extending portion of the L-shaped sternal rake extending under the sternum, and then retract the rib and the sternum together.

The Z-shape RULTRACT® retractor disclosed herein can achieve left or right internal mammary artery exposure at the undersurface of the chest wall for minimally invasive harvesting and grafting. This technique involves accessing the internal mammary artery at the level of the third or fourth intercostal region just below the third or fourth costal cartilage. Optionally, the surgeon may release and reflect the fourth or fifth costal cartilage downward or simply remove a two inch segment and reconstruct it with a single sternal wire at the end of the procedure. This opens up the fourth or fifth costal region and allows better visualization under the third or fourth costal cartilage, respectively.

The Z-shape retractor of the present invention provides two upward retraction points. The first is to retract the sternum vertically off the pericardial fat pad to help expose the undersurface of the sternal border. Once the internal mammary artery branches have been identified and the artery reflected off of the undersurface of the third costal cartilage, a single releasing incision is placed across the third costal cartilage directly lined with the internal mammary artery. The L-shaped rake is then placed under the third costal cartilage to achieve upward and cranial retraction of the released third costal cartilage towards the left shoulder. The Z-shape retractor of the present invention retracts both the sternum and third costal cartilage, which can then be retracted in unison using the cable and ratcheting retraction device. Individual adjustments of the sternal plate or the cartilage rake can be obtained by means of the threaded adjustment nuts 124 and the threaded portions 120 of the rakes.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A surgical retractor, comprising:
   a rake plate,
   at least one rake mounted with respect to the rake plate for applying a retractor force to a patient's body,
   wherein said rake plate has a generally Z-shape structure.

2. A surgical retractor as in claim 1, further comprising means for adjusting the extension of the at least one rake relative to the Z-shape rake plate.

3. A surgical retractor as in claim 1, wherein two rakes are mounted on the Z-shape rake plate.

4. A surgical retractor as in claim 1, wherein said at least one rake is pivotably mounted on the Z-shape rake plate.

5. A surgical retractor as in claim 1, wherein said Z-shape rake plate has a horizontal axis and the at least one rake is vertically adjustable with respect to the Z-shape rake plate.

6. A surgical retractor as in claim 5, wherein said at least one rake is pivotably mounted on the Z-shape rake plate for permitting the at least one rake to be adjusted relative to the rake plate.

7. A surgical retractor as in claim 6, wherein the legs of the Z-shape rake plate are substantially parallel and offset from one another.

8. A surgical retractor, comprising:
   a rake plate having a generally Z-shape structure;
   a rib rake adjustably mounted with respect to the rake plate for applying a retractor force to a patient's rib; and
   an L-shaped sternal rake adjustably mounted with respect to the rake plate for applying a retractor force to a patient's sternum.

9. A surgical retractor as in claim 8, wherein the L-shaped sternal rake includes a horizontally extending portion and an upwardly bent rake tip.

10. A surgical retractor comprising
    a Z-shape rake plate having a center portion and respective end portions,
    a mounting device to mount a respective rake in relative proximity to the respective end portions of the rake plate, and a clip for coupling a rake in relative proximity to the center portion of the rake plate.

11. A surgical retractor as set forth in claim 10, further including means for adjusting the extension of the rakes relative to the rake plate.

12. A method of holding open a surgical cavity comprising the steps of:

provviding a surgical cavity by making a surgical incision in a portion of a patient's body, attaching a first rake to a Z-shape rake plate, placing the first rake in the surgical incision, adjusting the extension of the first rake relative to the rake plate, and retracting the Z-shape rake plate together with the first rake to thereby retract the portion of the patient's body and provide access to the surgical cavity.

13. A method as set forth in claim 12, further comprising:

attaching a second rake to the Z-shape rake plate, placing the second rake in the surgical incision at a position for cooperation with the first rake, adjusting the extension of the second rake relative to the rake plate, retracting the Z-shape rake plate together with the first and second rakes to thereby retract the portion of the patient's body and provide access to the surgical cavity.

14. A method as set forth in claim 13, wherein the portion of the patient's body comprises an intercostal region of the patients rib cage.

15. A method as set forth in claim 14, wherein the first rake comprises a rib rake, and the step of placing the first rake includes placing the rib rake around a rib adjacent the surgical incision in the cranial direction.

16. A method as set forth in claim 15, wherein the second rake comprises an L-shaped sternal rake having as one of its legs a horizontally extending body-supporting portion, and the step of placing the second rake includes placing the L-shaped sternal rake laterally in the intercostal region so that the horizontally extending body-supporting portion extends under the sternum.

17. A method as set forth in claim 16, further comprising retracting the rib and sternum together.

18. A method of minimizing the space required in a surgical field for retraction, comprising using a Z-shape rake plate to support one or more rake mechanisms or the like, and adjusting the height position of at least one of the Z-shape rake plate or at least one or more rake mechanisms or the like to affect retraction.

* * * * *